US00PP25178P2

(12) United States Plant Patent
Kanaya et al.

(10) Patent No.: US PP25,178 P2
(45) Date of Patent: Dec. 16, 2014

(54) ***CALIBRACHOA* PLANT NAMED 'SUNBEL 208'**

(50) Latin Name: *Calibrachoa* sp.
Varietal Denomination: Sunbel 208

(71) Applicants: Takeshi Kanaya, Chiba (JP); Yasuyuki Murakami, Shiga (JP)

(72) Inventors: Takeshi Kanaya, Chiba (JP); Yasuyuki Murakami, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 101 days.

(21) Appl. No.: 13/815,124

(22) Filed: Jan. 31, 2013

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Susan McCormick Ewoldt
(74) *Attorney, Agent, or Firm* — C. A. Whealy

(57) ABSTRACT

A new and distinct cultivar of *Calibrachoa* plant named 'Sunbel 208', characterized by its mounding plant habit; vigorous growth habit; freely branching habit; early and freely flowering habit; long flowering period; relatively large bright purple violet-colored flowers; and good garden performance.

1 Drawing Sheet

Botanical designation: *Calibrachoa* sp.
Cultivar denomination: 'SUNBEL 208'.

BACKGROUND OF THE INVENTION

The present invention relates to a new and distinct cultivar of *Calibrachoa* plant, botanically known as *Calibrachoa* sp. and hereinafter referred to by the name 'Sunbel 208'.

The new *Calibrachoa* plant is a product of a planned breeding program conducted by the Inventors in Higashiomi, Shiga, Japan. The objective of the breeding program is to develop new mounding and freely branching *Calibrachoa* plants with numerous large and attractively colored flowers.

The new *Calibrachoa* plant originated from a cross-pollination conducted by the Inventors in Higashiomi, Shiga, Japan in October, 2009 of a proprietary selection of *Calibrachoa* sp. identified as code number T590-1, not patented, as the female, or seed, parent with a proprietary selection of *Calibrachoa* sp. identified as code number 7161-3, not patented, as the male, or pollen, parent. The new *Calibrachoa* plant was discovered and selected by the Inventors as a single flowering plant from within the progeny of the stated cross-pollination in a controlled greenhouse environment in Higashiomi, Shiga, Japan in July, 2010.

Asexual reproduction of the new *Calibrachoa* plant by vegetative cuttings in a controlled greenhouse environment in Higashiomi, Shiga, Japan since July, 2010 has shown that the unique features of this new *Calibrachoa* plant are stable and reproduced true to type in successive generations.

SUMMARY OF THE INVENTION

Plants of the new *Calibrachoa* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunbel 208'.

These characteristics in combination distinguish 'Sunbel 208' as a new and distinct *Calibrachoa* plant:

1. Mounding plant habit.
2. Vigorous growth habit.
3. Freely branching habit.
4. Early and freely flowering habit.
5. Long flowering period.
6. Relatively bright purple violet-colored flowers.
7. Good garden performance.

Plants of the new *Calibrachoa* can be compared to plants of the female parent selection. Plants of the new *Calibrachoa* differ primarily from plants of the female parent selection in the following characteristics:

1. Plants of the new *Calibrachoa* are smaller than plants of the female parent selection.
2. Plants of the new *Calibrachoa* and the female parent differ in flower color as plants of the female parent selection have deep blue-colored flowers.

Plants of the new *Calibrachoa* can be compared to plants of the male parent selection. Plants of the new *Calibrachoa* differ primarily from plants of the male parent selection in the following characteristics:

1. Plants of the new *Calibrachoa* are smaller than plants of the male parent selection.
2. Plants of the new *Calibrachoa* and the male parent selection differ in flower color as plants of the male parent selection have light pink-colored flowers.

Plants of the new *Calibrachoa* can also be compared to plants of *Calibrachoa* 'Suncalsifobu', disclosed in U.S. Plant Pat. No. 20,659. In side-by-side comparisons conducted in Higashiomi, Shiga, Japan, plants of the new *Calibrachoa* and 'Suncalsifobu' differed primarily in the following characteristics:

1. Plants of the new *Calibrachoa* were taller than plants of 'Suncalsifobu'.
2. Plants of the new *Calibrachoa* had longer internodes than plants of 'Suncalsifobu'.
3. Plants of the new *Calibrachoa* were more freely flowering than plants of 'Suncalsifobu'.

4. Plants of the new *Calibrachoa* had smaller flowers than plants of 'Suncalsifobu'.
5. Flowers of plants of the new *Calibrachoa* were darker in color than flowers of plants of 'Suncalsifobu'.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the top of the sheet comprises a side perspective view of a typical flowering plant of 'Sunbel 208' grown in a container.

The photograph at the bottom of the sheet is a close-up view of a typical flowering plant of 'Sunbel 208'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Calibrachoa* production. During the production of the plants, day temperatures averaged 23° C. and night temperatures averaged 13° C. Plants were four months old when the photographs and the description were taken. In the following description, color references are made to The Royal Horticultural Society Colour Chart, 2007 Edition, except where general terms of ordinary dictionary significance are used.

Botanical classification: *Calibrachoa* sp. 'Sunbel 208'.

Parentage:

*Female, or seed, parent*.—Proprietary selection of *Calibrachoa* sp. identified as code number T590-1, not patented.

*Male, or pollen, parent*.—Proprietary selection of *Calibrachoa* sp. identified as code number 7161-3, not patented.

Propagation:

*Type*.—By vegetative cuttings.

*Time to initiate roots, summer*.—About one week at 15° C. to 20° C.

*Time to produce a rooted young plant, summer*.—About three weeks at 15° C. to 20° C.

*Root description*.—Fibrous; white in color.

*Rooting habit*.—Freely branching.

Plant description:

*Plant and growth habit*.—Mounding plant habit; freely branching habit with numerous lateral branches developing per plant; pinching enhances lateral branch development; vigorous growth habit.

*Plant height*.—About 22 cm.

*Plant diameter*.—About 32 cm.

Lateral branch description:

*Length*.—About 25 cm.

*Diameter*.—About 1.6 mm.

*Internode length*.—About 1.25 cm.

*Strength*.—Strong.

*Aspect*.—Upright to outwardly.

*Texture*.—Pubescent.

*Color*.—Close to 144A.

Foliage description:

*Arrangement*.—Alternate, simple.

*Length*.—About 2.4 cm.

*Width*.—About 1.1 cm.

*Shape*.—Spatulate.

*Apex*.—Obtuse.

*Base*.—Cuneate.

*Margin*.—Entire.

*Texture, upper and lower surfaces*.—Pubescent.

*Venation pattern*.—Pinnate; reticulate.

*Color*.—Developing leaves, upper surface: Close to 143A. Developing leaves, lower surface: Close to 143C. Fully expanded leaves, upper surface: Close to 137B; venation, close to 144B. Fully expanded leaves, lower surface: Close to 137D; venation, close to 144C.

*Petiole*.—Length: About 3.1 mm. Diameter: About 1.2 mm. Texture, upper and lower surfaces: Pubescent. Color, upper and lower surfaces: Close to 144C.

Flower description:

*Flower arrangement and habit*.—Single salverform flowers arising from upper leaf axils; freely flowering habit with usually about 60 flowers developing per plant; flowers face upright or outwardly.

*Fragrance*.—None detected.

*Natural flowering season*.—Early flowering habit, plants of the new *Calibrachoa* initiate and develop flowers about three weeks after planting; long flowering period, flowering naturally commences during the spring and plants flower continuously throughout the summer until late autumn in Japan.

*Flower longevity*.—Individual flowers last about seven to ten days on the plant; flowers not persistent.

*Flower diameter*.—About 2.6 cm.

*Flower length (depth)*.—About 2.3 cm.

*Throat diameter*.—About 8 mm.

*Tube length*.—About 1.5 cm.

*Tube diameter, base*.—About 3.2 mm.

*Flower buds*.—Shape: Cylindrical. Length: About 1.9 cm. Diameter: About 4.1 mm. Color: Close to 77B.

*Corolla*.—Arrangement: Five petals fused at the base and opening into a flared trumpet. Petal length from throat: About 8.8 mm. Petal width: About 1.1 cm. Petal shape: Roughly spatulate. Petal apex: Rounded. Petal margin: Entire. Petal texture, upper and lower surfaces: Smooth, glabrous. Throat texture: Smooth, glabrous. Tube texture: Pubescent. Color: Petal, when opening, upper surface: Close to N82B; towards the throat, close to 77A. Petal, when opening, lower surface: Close to N82D. Petal, fully opened, upper surface: Close to N82C; towards the throat, close to 77A; venation, close to 187A. Petal, fully opened, lower surface: Close to N82D; venation, close to N82D. Throat: Close to 6A; venation, close to 152A. Tube: Close to 3C; venation, close to N77A.

*Calyx*.—Arrangement: One star-shaped tubular calyx tube with five sepals fused at the base. Sepal length: About 4.1 mm to 6.6 mm. Sepal width: About 2.6 mm. Sepal shape: Lanceolate. Sepal apex: Acute. Sepal margin: Entire. Sepal texture, upper and lower surfaces: Pubescent. Sepal color: Immature, upper and lower surfaces: Close to 144B. Mature, upper surface: Close to 143A. Mature, lower surface: Close to 143B.

*Peduncles*.—Length: About 8.1 mm. Diameter: About 0.8 mm. Angle: Upright to outwardly. Strength: Strong. Texture: Pubescent. Color: Close to 144C.

*Reproductive organs*.—Stamens: Quantity: Five per flower. Stamen length: About 6.3 mm to 8.6 mm. Anther shape: Ellipsoidal. Anther size: About 1.3 mm by 1.5 mm. Anther color: Close to 3D. Pollen amount: Moderate. Pollen color: Close to 4C. Pistils: Quantity: One per flower. Pistil length: About 1 cm. Style color: Close to 145D. Stigma shape: Transversely ellipsoidal. Stigma color: Close to 145C. Ovary color: Close to 145D.

*Seeds and fruits*.—Seed and fruit development have not been observed on plants of the new *Calibrachoa*.

Garden performance: Plants of the new *Calibrachoa* have been observed to have good garden performance and to tolerate wind, rain and temperatures ranging from about 5° C. to about 35° C.

Pathogen & pest resistance: Plants of the new *Calibrachoa* have not been observed to be resistant to pests and pathogens common to *Calibrachoa* plants.

It is claimed:

1. A new and distinct *Calibrachoa* plant named 'Sunbel 208' as illustrated and described.

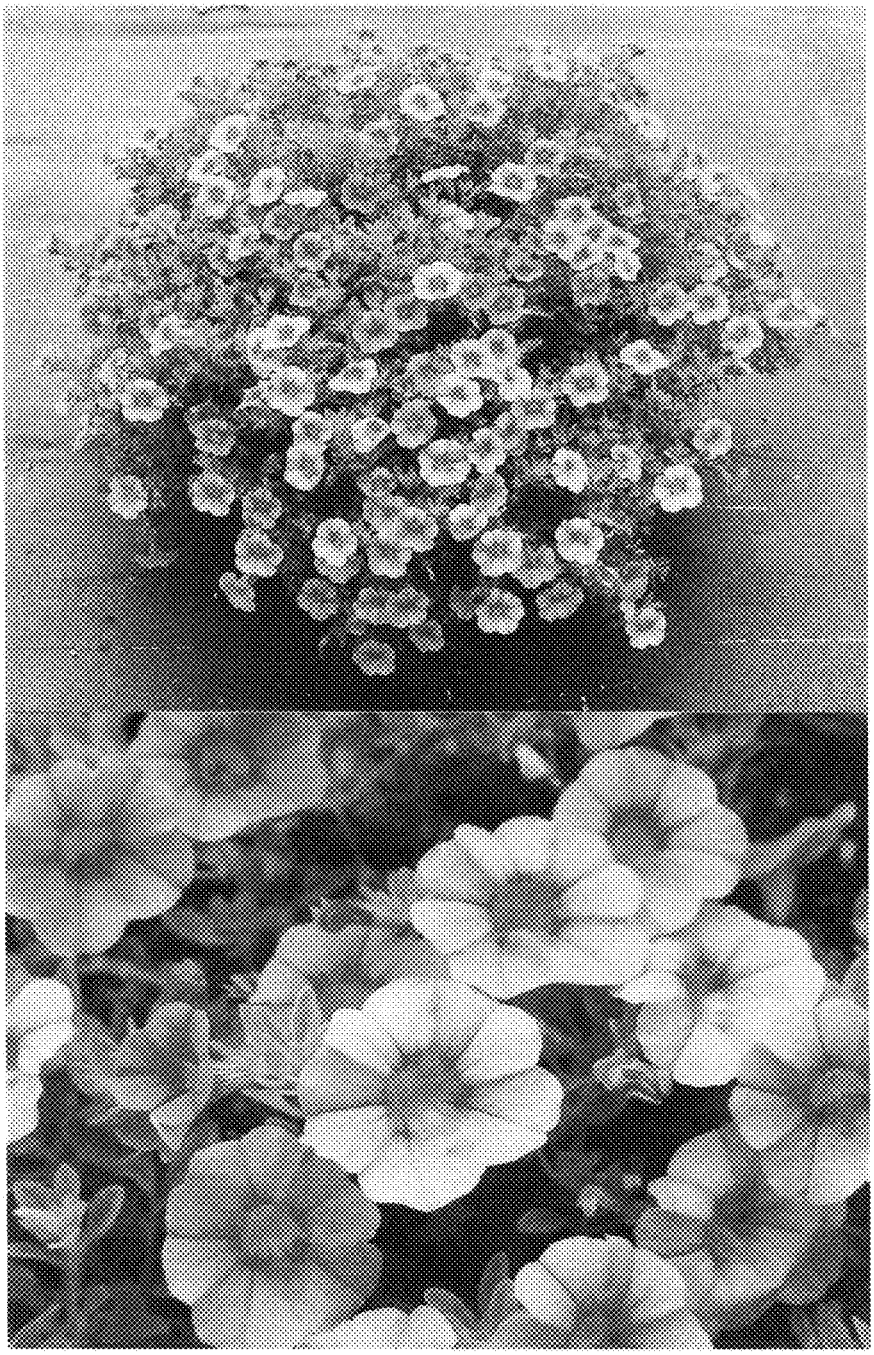

* * * * *